(12) United States Patent
Weng et al.

(10) Patent No.: US 7,601,535 B1
(45) Date of Patent: Oct. 13, 2009

(54) CELL CULTURE MEDIA FOR ENHANCED PROTEIN PRODUCTION

(76) Inventors: Steve Oh Kah Weng, Blk 286, #03-411, Bukit Batok East Ave. 3, Singapore 650286 (SG); Florence Chua nee Ho Kit Fong, Bioprocessing Technology Centre, National University of Singapore, 10 Kent Ridge Crescent, Singapore S119260 (SG)

( * ) Notice: Subject to any disclaimer, the term of this patent is extended or adjusted under 35 U.S.C. 154(b) by 0 days.

(21) Appl. No.: 10/264,979

(22) Filed: Oct. 4, 2002

Related U.S. Application Data

(63) Continuation-in-part of application No. 08/833,500, filed on Apr. 7, 1997, now abandoned.

(51) Int. Cl.
*C12N 5/06* (2006.01)
*C12N 5/08* (2006.01)

(52) U.S. Cl. .................. 435/383; 435/375; 435/404

(58) Field of Classification Search .............. 435/404, 435/383, 325
See application file for complete search history.

(56) References Cited

U.S. PATENT DOCUMENTS 3,950,547 A 4/1976 Lamar, III et al.
4,724,206 A * 2/1988 Rupp et al. ................. 435/69.1
4,767,704 A * 8/1988 Cleveland et al. .......... 435/70.2
5,122,469 A * 6/1992 Mather et al. ................ 435/383
5,316,938 A * 5/1994 Keen et al. ................... 435/404

OTHER PUBLICATIONS

Chua et al. "Enhanced IgG production in eRDF media with and without serum". Journal of Immunological Methods. 1994. 167:109-119.*
Chua, Florence K.F. et al., "Hyper-stimulation of monoclonal antibody production by high osomlarity stress in eRDF medium," *J. Biotechnology* vol. 37, pp. 265-275, 1994.
Murakami, Hiroki, "Serum-Free Media Used for Cultivation of Hybridomas", *Monoclonal Antibodies: Production and Application*, pp. 107-141, 1989.
Oh, Steve K.W. et al., "Intracellular Responses of Productive Hybridomas Subjected to High Osmotic Pressure", *Biotechnology and Bioengineering*, vol. 46, pp. 525-535, 1995.

* cited by examiner

*Primary Examiner*—Vera Afremova
(74) *Attorney, Agent, or Firm*—DLA Piper LLP (US)

(57) ABSTRACT

Culture media for in vitro cell culture which contain substantially saturated amounts of selected amino acids improve protein production, constrain cell growth and extend cell longevity, methods for the production and use of such media, and systems for the production of protein utilizing such media and methods.

14 Claims, 9 Drawing Sheets

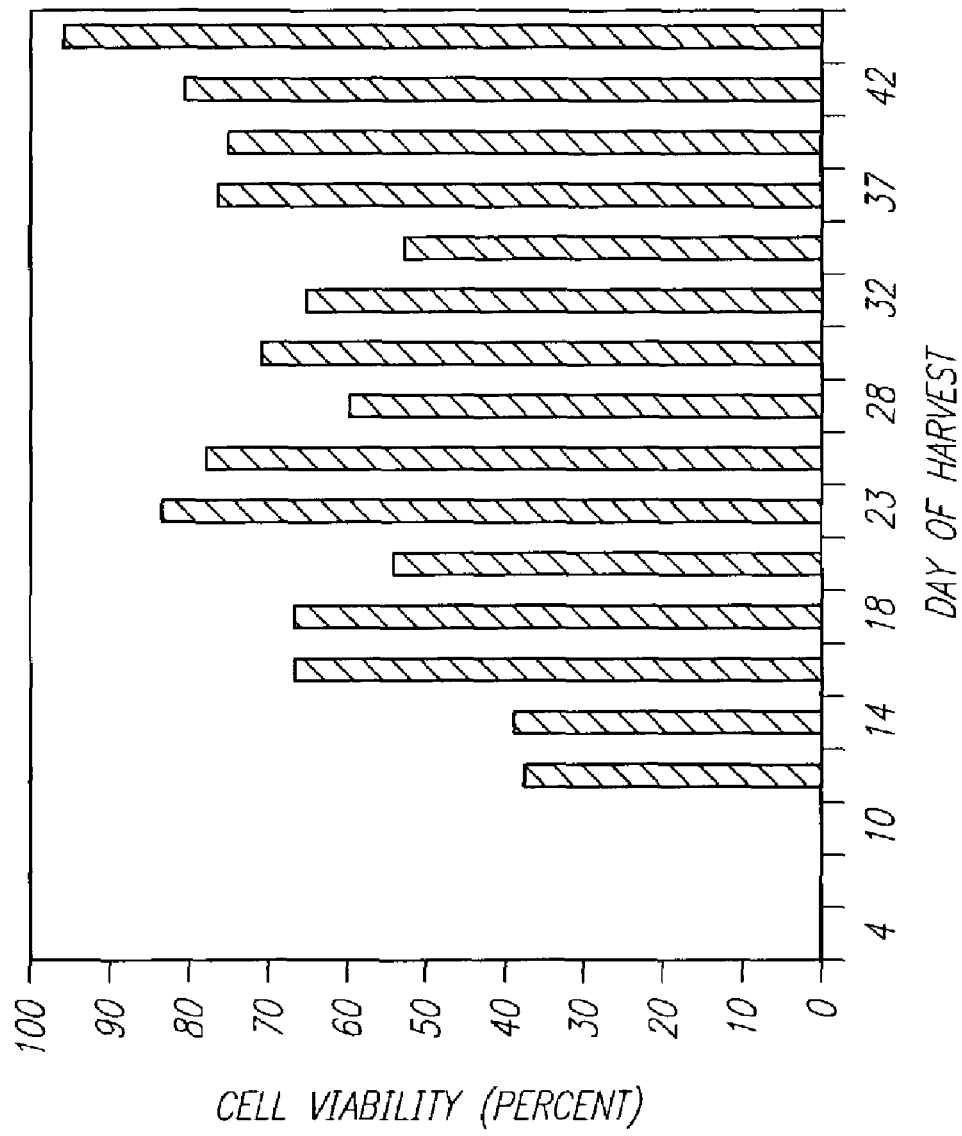

CELL CULTURE MEDIA FOR ENHANCED PROTEIN PRODUCTION

RELATED APPLICATION DATA

This application is a continuation-in-part of commonly owned U.S. patent application Ser. No. 08/833,500, filed Apr. 7, 1997 now abandoned.

TECHNICAL FIELD

The present invention is directed to culture media for in vitro cell culture which improve protein production, constrain cell growth and extend cell longevity, and to methods for the production and use of such media.

BACKGROUND OF THE INVENTION

The increasing demand for monoclonal antibodies (MABs) useful in research, diagnosis, therapy, and purification purposes has created a need to optimize protein production techniques. The prior art includes improved bioreactor designs and bioreactor operation to increase cell densities or the longevity of the cell culture by nutrient feedings.

Bioreactors have been operated in fed-batch, immobilized, perfusion and continuous modes. Alternate strategies, such as the use of temperature, media formulation, including the addition of mouse peritoneal factors, growth inhibitors, autocrine factors or cyclic mononucleotides and hyperstimulation by osmolarity stress, have been used to enhance protein production. These approaches have shown only marginal success.

Commonly used basal cell culture media are RPMI 1640, DMEM (Dulbecco's modified Eagle's medium), Ham's F12 and DMEM/F12 (DF). A modified medium, eRDF, prepared from RDF (RPMI:DMEM:F12, 2:1:1) by enrichment with amino acids, glucose and vitamins, was described by Murakami, H. (1989) "Serum-free media used for cultivation of hybridomas." In: A. Mizrahi (Ed.), Advances in Biotechnological Processes, Vol. 11, Monoclonal Antibodies: Production and Application. Alan R. Liss, New York, pp. 107-141. Murakami showed that doubling the total amino acids or glucose alone in the culture medium did not increase cell density, but concurrent elevation of amino acids and glucose maximized the cellular growth by threefold.

Hyper-stimulation of monoclonal antibody production by high osmolarity stress in an eRDF medium is described in Chua, F., et al. (1994) *J. Immunological Methods* 167:109-119, and Chua, F., et al. (1994) *J. Biotechnology* 37:265-275. However, the maximum IgG concentration achieved was about 300 μg/mL and 270 μg/mL for HG11 and TBC3 cells, respectively, at medium osmolarities about 350 to 400 mOsm. Further increase in osmolarity of the therein-described media with NaCl caused deterioration in antibody production.

Oh, S. K. W., et al. ((1995) *Biotechnology and Bioengineering* 48:525-535) report that hybridomas increased metabolic activities and amino acids uptake via the $Na^+$ dependent symports to compensate for the osmotically elevated external environment.

Oh, S. K. W., et al. ((1996) "Flow Cytometric Studies of Osmotically Stressed and Sodium Butyrate-Treated Hybridoma Cells" in Flow Cytometry Applications in Cell Culture, Marcel Dekker, Inc., (Eds. M. Al-Rubeai and A. N. Emergy) New York, Base1, Hong Kong, pp. 101-119) also describes the application of flow cytometry in examining the relationships between total cellular monoclonal antibody content, cell size, and cell cycle distribution of hybridomas subjected to environmental stress.

DISCLOSURE OF THE INVENTION

The present invention provides methods and compositions for cell culture nutrient media which improves protein production, constrains cell growth and extends cell longevity.

In one aspect, the invention provides a cell culture medium for maintaining and proliferating cultured cells in vitro and the production of protein therefrom. The media comprises an aqueous solution comprising an amino acid component comprising at least one essential amino acid in its individual substantially saturated concentration in the aqueous solution when the aqueous solution is maintained at a temperature in the range of 30° to 50° C., and a basal medium component comprising such mineral salts, carbohydrates, nucleic acids, vitamins, lipids, and other compounds as are necessary to the viability and proliferation of cultured cells in vitro.

In certain embodiments of the invention, the dry weight of the amino acid component of the aqueous solution comprises at least 20% of the total dry weight of all solid constituents contained in the medium. Also in certain embodiments of the invention, the osmolarity of the aqueous solution is from approximately 320 to 450 mOsm.

Other aspects of the present invention provide methods for preparing media of the present invention, methods for culturing cells in vitro and systems for the production of proteins utilizing the media of the invention.

BRIEF DESCRIPTION OF THE DRAWINGS

FIGS. 2A-D graphically depict the results of hollow fiber bioreactor examples in which medium BTC-28101 was utilized as the cell culture medium, wherein FIG. 2A displays the levels of antibody produced by cell cultures over time, FIG. 2B depicts pH variations for the medium over time, FIG. 2C depicts the glucose utilization over time, and FIG. 2D displays cell viability over time;

FIG. 3B graphically depicts IgG concentration produced from hybridoma 2HG11 grown in serum-free BTC-28101 and commercial media Hb and PFHM available from Gibco;

DETAILED DESCRIPTION OF THE INVENTION

Figure 1:
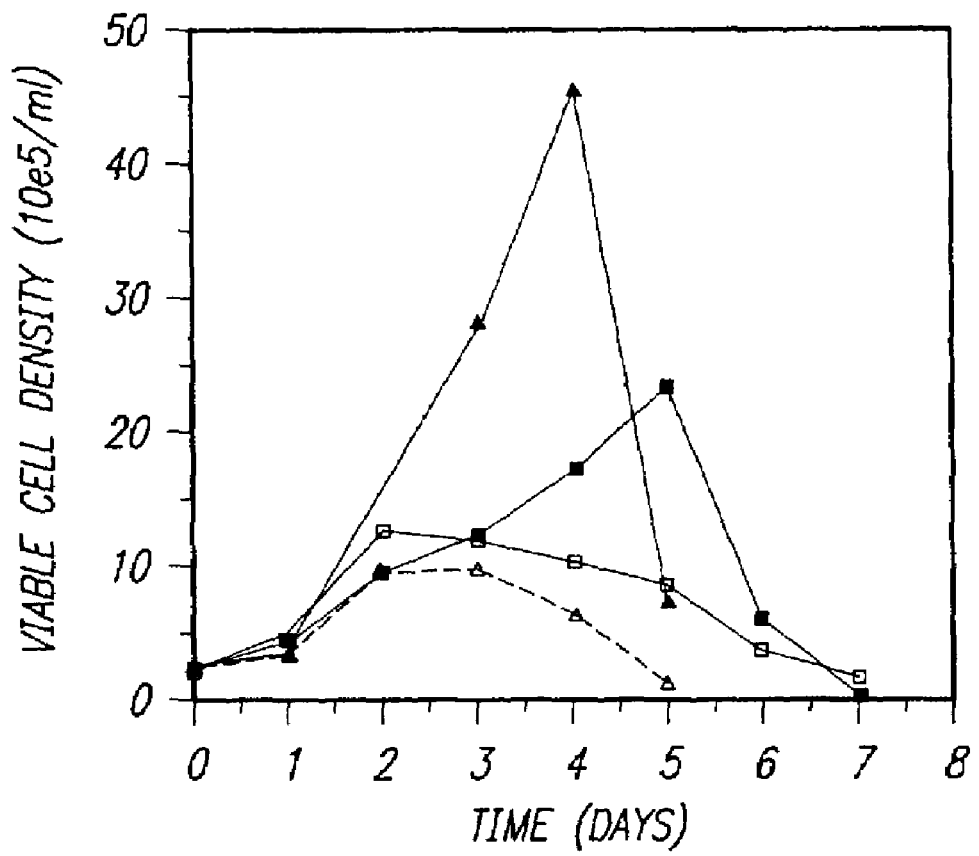
FIG. 1 graphically depicts the growth of hybridomas 2HG11 and TBC3 in medium BTC-28101 of the invention and in control medium DMEM/F12.

The present invention provides methods and compositions for cell culture nutrient media which improves protein production, constrains cell growth and extends cell longevity.

In one aspect, the invention provides a cell culture medium for maintaining and proliferating cultured cells in vitro and the production of protein therefrom. The media comprises an aqueous solution comprising an amino acid component comprising at least one essential amino acid in its individual substantially saturated concentration in the aqueous solution when the aqueous solution is maintained at a temperature in the range of 30° to 50° C., and a basal medium component comprising such mineral salts, carbohydrates, nucleic acids, vitamins, lipids, and other compounds as are necessary to the viability and proliferation of cultured cells in vitro.

In the present description, the following terms will have the indicated definitions, unless a contrary definition is evident from the context in which the term is used.

As used herein, the term "cell culture medium" refers to any nutrient medium in which cells of any type may be cultured in vitro.

As used herein, the term "bioreactor" refers to any device in which cells may be cultured. Includes stationary flasks, spinner flasks and hollow fiber bioreactors.

As used herein, the term "basal medium" refers to any cell culture medium that contains all of the ingredients essential to cell metabolism, e.g., amino acids, lipids, carbohydrates, vitamins and mineral salts. RPMI, DMEM, Ham's 12, and eRDF are examples of basal media.

As used herein, the term "essential amino acid" refers to those amino acids not produced endogenously (or because it or a critical precursor is not produced in sufficient quantity to sustain cell growth, longevity and protein production) by cellular metabolism of cells. Although the list of amino acids defined as essential varies widely depending upon the cell type, for most types of mammalian cells in culture such amino acids are generally recognized to include arginine (Arg), cysteine (Cys), glutamine (Gln), histidine (His), isoleucine (Ile), leucine (Leu), lysine (Lys), methionine (Met), phenylalanine (Phe), proline (Pro), threonine (Thr), tryptophan (Trp), tyrosine (Tyr), and valine (Val). Of this list, cysteine, glutamine, proline and tyrosine are the amino acids most frequently defined as non-essential, depending upon the particular cell type in culture. For example, tyrosine is a non-essential amino acid in albino rat cells, but its synthesis requires the essential amino acid phenylalanine. Likewise, cysteine requires methionine, and proline and glutamine require glutamic acid.

As used herein, the term "non-essential amino acid" refers to those amino acids produced endogenously by cells in sufficient quantity to sustain cell growth, longevity and protein production. Although the list of amino acids defined as non-essential varies widely depending upon the cell type, for mammalian cells in culture such amino acids are generally recognized to include alanine (Ala), asparagine (Asn), aspartic acid (Asp), glutamic acid (Glu), glycine (Gly), and serine (Ser), with the recognized qualifications outlined previously.

As used herein, the term "DMEM/F12" refers to a mixture of Dulbecco's Modified Eagle's Medium and Ham's F12 in 1:1 proportions).

As used herein, the term "substantially saturated" refers to the limits of solubility for a particular substance as a component of the cell culture medium under particular physical conditions such as temperature. Solubility refers to the mass of the substance contained in the liquid; when this mass is at equilibrium with an excess of the substance, the solution is said to be saturated. Substantially saturated is therefore taken to mean approximately the point at which the substance will precipitate out of solution (or will not continue to dissolve) under the defined physical conditions.

General Features of the Media

The invention provides media and methods for improving protein production in cultures of protein producing cells, as well as an improved protein production system. In particular, the invention comprises culturing cells, including hybridomas and other antibody producing cells, as well as cells producing recombinant proteins, in an aqueous medium comprising a high concentration of amino acids, in particular the essential amino acids for a chosen cell type, and typically an energy source such as glucose or sucrose. The medium is substantially saturated at around 40° C. with an amino acid or mixture of amino acids essential to the metabolism of the cultured cells. The medium of the invention can contain approximately 5.50 to approximately 20 grams per liter of total or gross amino acids in solution or suspension and, in addition, approximately 5.50 to approximately 20 grams per liter of a carbohydrate energy source, preferably glucose, in solution. The gross amino acids content of the present media desirable comprise at least 20%, and preferably from about 25% to about 50%, of the total dry weight of the medium components. The present media will typically display a high level of osmolarity, and the cells may appropriately be adapted to the high osmolarity media of this invention by passaging.

A unique feature of the present media is that, by providing a maximized amount of certain media components by substantially saturating the aqueous solution, an adequate supply of nutrients is maintained from the initiation of the culture.

Increasing the concentrations of the selected media components inevitably increases the osmolarity, to a point far in excess of that found in most prior art basal media. The osmolarity of the present media is generally from approximately 320 to approximately 450 mOsm. Sodium chloride is the preferred osmolyte in the event it is desired to increase the osmolarity of the present media beyond that established by the various media components.

The media and the methods of the invention are useful in all forms of bioreactors. The benefits of the invention are realized in static, batch, shaker flask, and spinner flask and hollow fiber bioreactor culture procedures. Of particular benefit is the use of the present media in batch mode, which can be performed with less user intervention than fed-batch cultures.

Amino Acid Uptake and Metabolism

Amino acid transport regulation in animal cells is controlled by both sodium ion ($Na^+$) dependent and independent transport systems. The $Na^+$ dependent group consists of systems A, ASC, N, Gly, and β. Both systems A and ASC are ubiquitous in mammalian cells. It is reported that the primary mechanism for uptake of amino acids by cells is via sodium ion ($Na^+$) dependent transport systems, including cell transport system A. System A is primarily responsible for the increased uptake of amino acids in high osmolarity media, and this effect is enhanced where $Na^+$ ions are a substantial part of the osmolarity of the media. Thus, in the media of the present invention, it is desirable that one or more of the amino acids present in substantially saturated concentration be reactive with cell transport system A.

In addition, where it is deemed desirable to increase the osmolarity of the media beyond that provided by the various amino acids and basal media constituents, then sodium chloride would be the preferred osmolyte. At the same time, it is desirable that the ratio of $Na^+$ ions to potassium ions ($K^+$) be maintained at approximately normal levels (e.g. 20:1), in order to optimize amino acid uptake.

As discussed below, the media of the present invention appear, under certain circumstances, to allow the cultured cells to derive a significant portion of their energy requirements from sources other than the traditional carbohydrates such as glucose. The amino acids of the present media can serve as a preferential energy source for cell metabolism, thus reducing the reliance of the cells on supplied carbohydrates in the media.

Media Components

In order to provide a cell culture medium in accordance with the present invention, the various constituents recognized as constituting the requirements for a basal medium must be addressed. These constituents typically include amino acids, inorganic mineral salts, energy sources such as carbohydrates and other carbon sources, vitamins and co-factors, nucleic acids and derivatives, lipids and derivatives, as well as buffers and, typically, visual pH indicators to facilitate the monitoring of the cell culture medium. It is well known that animal cells have a need for certain ionic, nutrient, matrix protein attachment and growth factors in order to thrive. These elements are related to the requirements for growth and development.

The inorganic salts in culture media have two major functions. First, salt concentrations are ordinarily adjusted to approach the natural salt concentration levels from which the cells are derived. This is to minimize any deviation in osmotic pressure on the cells that would require energy consuming ionic pumps to maintain cellular integrity. In the present invention, these considerations are subsumed to the overriding goal to increase protein production.

Secondly, these salts include many ions which are utilized as enzymatic cofactors and intracellular messengers. Often, for some ions to be effectively transported into the cell, additional carrier molecules are needed in the medium. For example, in mammalian cell culture systems, transferrin is a carrier of iron.

As mentioned previously, although most mammalian cell culture media utilize glucose as the main carbon source, and although the present media likewise contain at least one carbohydrate, such as glucose, typically comprising a total of from approximately 5.5 to approximately 20 grams per liter in the medium, it has been found that, under certain circumstances, the media of the present invention may promote the utilization of alternative sources for carbon and energy. For example, the glucose of the present media does not serve as an energy source in the same manner as it does in conventional media (see Example 7 and FIG. 2C). These data indicate that the cells cultured in the present media shift from normal glycolysis to an alternative pathway. There is no indication that such a phenomenon would occur in any of the known prior art media. However, it is also noted that the cell cultures in the present system typically performed best when carbohydrate, such as glucose, was supplied in sufficient quantity so that it did not become depleted during the course of cell culture.

It is known that many animal cells grow best when attached to natural substrates like collagen, laminin, and fibronectin. It has been shown that the addition of ascorbic acid to cell culture medium increased the production and deposition of collagen by mammalian cells. See Engvall, E., et al. *J. Cell Biol.* (1986) 102:703-710. The production of collagen by cells in culture helps to create a natural matrix for growth. In a general basal media it is very difficult to define all the requirements that animal cells need for growth and protein production. Thus, the use of bovine or fetal bovine serum as a supplement in mammalian culture systems, has become a well accepted means of supplying various supplementary factors, the precise nature and requirements of which are not always capable of rigorous determination.

In the present invention, the utilization of media which is substantially saturated with various amino acid constituents, more typically at least one of the essential amino acids for a particular cell culture, has proven to be desirable in order to improve protein production, constrain cell growth and extend cell longevity. In addition, it is particularly preferred to supply at least all of the essential amino acids for a particular cell culture, and desirably all twenty recognized amino acids, as well as hydroxyproline and cystine, desirably all in each of the amino acid's individual substantially saturated concentration, in order to optimize protein production. It has been found to be desirable to include both cystine and cysteine in the present media, in spite of the fact that cysteine is more readily soluble and utilizable by cells in culture, as at the high concentrations utilized herein cysteine can display cytotoxic properties. Thus, the presence of cystine in the present media ensures an adequate supply of cysteine for cell growth and protein production, without the cytotoxic effects.

As stated above, the media of the invention will desirably contain approximately 5.50 to approximately 20 grams per liter of total or gross amino acids in solution, and the gross amino acids content of the present media desirable comprise at least 20%, and preferably from about 25% to about 50%, of the total dry weight of the medium constituents.

It will also be found useful to include an undissolved suspension of at least one of the amino acids in certain embodiments of the present media. In this manner the substantially saturated concentration of the amino acid is maintained in the aqueous solution of the media as the cell metabolism consumes the amino acid dissolved in solution.

Formulation and Production of Media

In view of the substantially saturated content of various substances of the present media, it is considered desirable to formulate the media in a manner that simplifies the dissolution of the various media constituents. One means of accomplishing this task is to formulate the various media constituents into components, or mixtures of dry powders, and bring such media components into solution either separately or in a step-wise fashion. In addition, heating the solution to temperatures above the range at which the solution will be utilized as cell culture media (typically a range of temperatures considered physiological) will also aid in the dissolution of the solid constituents, and in rendering the media substantially saturated at the designated temperature range. For example, the present media will typically be used at temperatures approximating 35-38° C. Thus, it may be desirable to saturate the medium with, e.g., the selected amino acid constituent by dissolving the constituent at a temperature in excess of the cell culture temperature so that the constituent will dissolve to a higher concentration, ordinarily while the aqueous solution is maintained in the range above 38° C., for example in the range of 40-50° C. In that manner, the aqueous solution may be substantially saturated, and depending upon the various physical conditions, the saturating constituents will be at approximately the point at which the constituents will precipitate out of solution (or will not continue to dissolve). When the temperature of the medium is then reduced for storage, e.g. typically to approximately 4° C., the solubility of the constituent in the medium is maintained, and the amino acid constituent does not then come out of solution.

In this manner also, the present media can be provided with an undissolved suspension of such constituents, such as at least one of the essential amino acids, in the aqueous solution. This permits maintenance of a substantially saturated concentration of the constituent in the aqueous solution as the cell metabolism consumes the constituent dissolved in solution. Ordinarily, the present media will be stored at ambient temperatures, such as room temperature or even refrigerated, below the temperatures employed for cell culture. Thus, the present media in storage will likely be super-saturated for one or more constituents, or an excess of undissolved constituent will likely be present under storage conditions.

Cell Cultures

Cells of any kind may be cultured in any of the methods of the invention. Cultures of antibody-producing cells, including hybridomas and other antibody producing cells, will derive particular benefit from the cell culture media of the present invention. The means to obtain such antibody-producing cell cultures are well known in the art. Hybridoma cell cultures, for example, are obtained by resort to the technology developed since the seminal work of Kohler and Milstein (1976).

Culture of recombinant protein-expressing mammalian cells, e.g., CHO cells, BHR cells, COS cells, Namalwa cells and the like, is an aspect of the invention. Many types of mammalian cells, which contain recombinant protein expression vectors, are well known in the art. See, e.g.:

Acklin, C., et al. "Recombinant human brain-derived neurotrophic factor (THuBDNF). Disulfide structure and characterization of BDNF expressed in CHO cells," *Int. J. Pept. Protein Res.* (1993) 41: 548-52;

Fukushima, K., et al., "N-linked sugar chain structure of recombinant human lymphotoxin produced by CHO cells; the functional role of carbohydrate as to its lectin-like character and clearance velocity," *ABB* (1993) 304:144-53;

Hayakawa, T., et al., "In vivo biological activities of recombinant human erythropoietin analogs produced by CHO cells, BHK cells and C127 cells," *Biologicals* (1992) 7:139-50;

Langley, K. E., et al., "Purification and characterization of soluble forms of human and rat stem cell factor recombinantly expressed by *Escherichia coli* and by Chinese hamster ovary cells," *ABB* (1992) 295:21-8;

Lu, H. S., et al., "Post-translational processing of membrane-associated recombinant human stem cell factor expressed in Chinese hamster ovary cells," *ABB* (1992) 298:150-8;

Malik, N., et al., "Amplification and expression of heterologous oncostatin M in Chinese hamster ovary cells," *DNA Cell Biol.* (1992) 11:453-9;

Nagao, M., et al., "Production and ligand-binding characteristics of the soluble form of murine erythropoietin receptor," *Biochem. Biophys. Res. Commun.* (1992) 188:888-97;

Rice, K. G., et al., "Quantitative mapping of the n-linked sialyloligosaccharides of recombinant erythropoietin; combination of direct high-performance anion-exchange chromatography and 2-aminopyridine derivatization," *Anal. Biochem.* (1992) 206:278-87;

Schmelzer, C. H., et al., "Purification and partial characterization of recombinant human differentiation-stimulating factor," *Protein Expr. Purif.* (1990) 1:54-62;

Schmelzer, C. H., et al., "Biochemical characterization of human nerve growth factor," *J. Neurochem.* (1992) 59:1675-83;

Sima, N., et al., "Tumor cytotoxic factor/hepatocyte growth factor from human fibroblasts; cloning of its cDNA, purification and characterization of recombinant protein," *Biochem. Biophys. Res. Commun.* (1992) 180:1151-8;

Sun, X. J., et al., "Expression and function of IRS-1 in insulin signal transmission," *J. Biol. Chem* (1992) 267:22662-72;

Suzuki, A., et al., "Biochemical properties of amphibian bone morphogenetic protein-4 expressed in CHO cells," *BJ* (1993) 291:413-7;

Tressel, T. J., et al., "Purification and characterization of human recombinant insulin-like growth factor binding protein 3 expressed in Chinese hamster ovary cells," *Biochem. Biophys. Res. Commun.* (1991) 178:625-33;

Lucas, B. K., et al., "High-level production of recombinant proteins in CHO cells using dicistronic DHFR intron expression vector," *Nucleic Acids Res.* (1996) 24:1774-9.

As the present media includes features which differ from those ordinarily found in the physiological environment from which the cultured cells were derived, it has been found to be beneficial to cell growth and longevity, and particularly to protein production, to adapt the cell cultures to the present media. This adaptation is typically accomplished by a period of passaging, or re-establishing the culture anew in fresh media, in accordance with well-known principles. Typically, such adaptation will be accomplished by daily passaging, e.g. at approximately $2 \times 10^5$ cells/mL, and will be continued for a period of time until the viability of the inoculum culture is in excess of 90% before the protein-producing culture is established. Such adaptation can also be accomplished by passaging the cells through a series of media of ever-increasing osmolarity, such as 250 mOsm, 300 mOsm, 350 mOsm, 400 mOsm, and the like, naturally leading up to adaptation of the cultured cells to the osmolarity of the particular medium to be employed for protein production culture.

The invention having now been generally described, the same will be better understood by reference to the following detailed examples, which are provided for illustration and are not to be considered as limiting the invention unless so specified.

EXPERIMENTAL

In the experimental disclosure which follows, all weights are given in grams (g), milligrams (mg), micrograms (µg), nanograms (ng), or picograms (pg), all amounts are given in moles (mol), millimoles (mmol), micromoles (µmol), nanomoles (nmol), picomoles (pmol), or femtomoles (fmol), all concentrations are given as percent by volume (%), proportion by volume (v:v), molar (M), millimolar (mM), micromolar (µM), nanomolar (nM), picomolar (pM), femtomolar (fM), or normal (N), all volumes are given in liters (L), milliliters (mL), or microliters (µL), and linear measurements are given in millimeters (mm), or nanometers (nm) unless otherwise indicated.

EXAMPLE 1

Preparation of Medium BTC-28101

A dry powder form of Medium BTC-28101 was prepared as two separate components (A) and (B) as listed in Table I. The ingredients were milled to fine dry powder prior to use. To prepare the medium, Component (A) was dissolved in 90% by volume of pyrogen-free water. The mixture was warmed to around 40° C. and stirred for one hour to fully dissolve the powder and then cooled to room temperature. Component (B) was added and stirred another hour to dissolve. The pH was adjusted to 7.0 by addition of NaOH. Water was added to make up the desired volume. The osmolarity of the medium was in the range of 330-335 mOsm.

TABLE I

Composition of Medium BTC-28101 in mg/L

Component (A)

Amino Acids

| | | | |
|---|---|---|---|
| Alanine | 13.4 | Arginine HCl | 1,162.9 |
| Asparagine · $H_2O$ | 189.2 | Aspartic acid | 80.0 |
| Cystine · 2HCl | 105.4 | Cysteine HCl · $H_2O$ | 105.4 |
| Glutamic acid | 79.4 | Glutamine | 1,997.2 |
| Glycine | 85.6 | Histidine HCl · $H_2O$ | 150.9 |

TABLE I-continued

Composition of Medium BTC-28101 in mg/L

| Hydroxyproline | 63.0 | Isoleucine | 314.8 |
|---|---|---|---|
| Leucine | 330.6 | Lysine HCl | 394.6 |
| Methionine | 98.4 | Phenylalanine | 148.6 |
| Proline | 110.6 | Serine | 170.2 |
| Threonine | 221.6 | Tryptophan | 36.8 |
| Tyrosine | 174.0 | Valine | 218.0 |

Component (B)

Mineral Salts

| $CaCl_2$ (anh) | 82.1 |
|---|---|
| $CuSO_4 \cdot 5H_2O$ | 0.00075 |
| $FeSO_4 \cdot 7H_2O$ | 0.220 |
| KCl | 372.8 |
| $MgSO_4$ (anh) | 52.4 |
| NaCl | 6,136.2 |
| $Na_2HPO_4$ (anh) | 484.1 |
| $ZnSO_4 \cdot 7H_2O$ | 0.23 |

Vitamins

| Biotin | 0.102 |
|---|---|
| D-Ca panthothenate | 1.240 |
| Folic acid | 8.800 |
| Putrescine · 2HCl | 0.040 |
| Niacinamide | 1.510 |
| Para-aminobenzoic acid | 0.510 |
| Pyridoxine HCl | 0.520 |
| Pyridoxal HCl | 1.000 |
| Riboflavin | 0.210 |
| Thiamine HCl | 1.585 |
| Vitamin $B_{12}$ | 0.342 |

Carbohydrates and derivatives

| D-Glucose | 6,846.0 |
|---|---|
| Na Pyruvate | 110.0 |

Nucleic acid derivatives

| Thymidine | 5.7 |
|---|---|
| Hypoxanthine | 1.0 |

Lipids and derivatives

| Choline bitartrate | 55.7 |
|---|---|
| i-Inositol | 104.5 |
| Linoleic acid | 0.020 |
| Lipoic acid | 0.050 |

Thiol compound

| Glutathione (reduced) | 0.490 |
|---|---|

Buffers

| HEPES | 3,570.0 |
|---|---|
| $NaHCO_3$ | 1,130.0 | pH indicator

| Phenol red | 6.0 |
|---|---|

The composition of the medium BTC-28101 was:

| Glucose (g/L) | 6.846 |
|---|---|
| Amino acids (g/L) | 6.251 |
| Amino acids (% d.w.*) | 24.8 |

*dry weight of media ingredients

EXAMPLE 2

Effect of Medium BTC-28101 on Cell Growth, Viability and IgG Production

This example compares cell growth and monoclonal antibody production in two hybridoma cell lines 2HG11 (anti-human chorionic gonadotropin) and TBC3 (anti-human IgG) in the serum supplemented BTC-28101 medium of Example 1 versus DMEM/F12.

The cultures were established in shaker flasks with 100 mL media supplemented with 10% Fetal Bovine Serum (FBS). Inoculum cells were adapted and maintained by daily passaging at $2\times10^5$ cells/mL with the respective fresh medium for at least a week, and the viability of each inoculum culture was above 90% before use. Batch culture was started by inoculating the cells at $2\times10^5$ cells/mL into the respective medium. Samples were taken daily to follow the cell growth by trypan blue staining and hemocytometer counting. Monoclonal antibody concentration in the culture supernatant was determined by ELISA analysis. The effect of the present media on cell growth is shown in FIG. 1. The maximum concentrations of Ig produced at the end of the cultures are summarized in Table II:

TABLE II

Maximum Ig Concentration in Cell Cultures with BTC-28101 and Control DMEM/F12 Media

| | Max Ig Concentration (μg/mL) | |
|---|---|---|
| Cell Line | DMEM/F12 | BTC-28101 |
| 2HG11 | 50 | 270 |
| TBC3 | 84 | 450 |

EXAMPLE 3

Effect of Medium BTC-28101 on Cell Growth, Viability and Ig Production

Hybridoma cell line TH12 (anti-theophylline) was cultured in either the BTC-28101 media of Example 1 or a DMEM formulation. Cells were inoculated into 100 mL of BTC-28101 or control medium DMEM at $2\times10^5$ cells/mL in 250 mL spinner flasks, both media were supplemented with 10% FBS. Similar procedures as stated in Example 2 were followed for preparing the inoculum cultures, and for monitoring the batch. TH12 produced higher concentrations of antibody in BTC-28101 than in the formulation of DMEM. As Table III shows, cell numbers and cell viability were also higher in BTC-28101.

TABLE III

TH12 Batch Culture: Cell Counts and Viabilities

| TIME | MEDIUM | CELL COUNT | VIABILITY |
|---|---|---|---|
| $D_0$ | BTC-28101 | $2 \times 10^5$/mL | 100% |
| | DMEM | $2 \times 10^5$/mL | 90% |
| $D_1$ | BTC-28101 | $5.6 \times 10^5$/mL | 100% |
| | DMEM | $2.6 \times 10^5$/mL | 100% |
| $D_2$ | BTC-28101 | $2.4 \times 10^6$/mL | 98% |
| | DMEM | $0.8 \times 10^6$/mL | 91% |
| $D_3$ | BTC-28101 | $3 \times 10^6$/mL | 98% |
| | DMEM | $2.2 \times 10^6$/mL | 97% |
| $D_4$ | BTC-28101 | $3.4 \times 10^6$/mL | 93% |
| | DMEM | $1.4 \times 10^6$/mL | 77% |
| $D_5$ | BTC-28101 | $3.8 \times 10^6$/mL | 69% |
| | DMEM | $0.5 \times 10^6$/mL | 32% |
| $D_6$ | BTC-28101 | $8.4 \times 10^5$/mL | 25% |
| | DMEM | $3.6 \times 10^5$/mL | 20% |
| $D_7$ | BTC-28101 | | <5% |
| | DMEM | | <5% |

Viabilities in both media were <5%.

Total media volumes collected for analyses.

Table IV demonstrates enhanced Ig production and specific antibody titer when BTC-28101 is used.

TABLE IV

TH12 Batch Culture: Ig Concentrations and Specific Antibody Titers

| TIME | MEDIUM | Ig mg/ML[1] | TITER[2] |
|---|---|---|---|
| $D_1$ | BTC-28101 | 539 µg/mL | 1,600 |
|  | DMEM | 447 µg/mL | 400 |
| $D_2$ | BTC-28101 | 468 µg/mL | 12,800 |
|  | DMEM | 397 µg/mL | 3,200 |
| $D_3$ | BTC-28101 | 681 µg/mL | 12,800 |
|  | DMEM | 440 µg/mL | 6,400 |
| $D_4$ | BTC-28101 | 752 µg/mL | 6,400 |
|  | DMEM | 518 µg/mL | 3,200 |
| $D_5$ | BTC-28101 | 823 µg/mL | 25,600 |
|  | DMEM | 553 µg/mL | 6,400 |
| $D_6$ | BTC-28101 | 1,500 µg/mL | 25,600 |
|  | DMEM | 489 µg/mL | 6,400 |
| $D_7$ | BTC-28101 | 1,190 µg/mL | 25,600 |
|  | DMEM | 560 µg/mL | 3,200 |

[1]Ig concentrations determined by precipitating each sample with saturated ammonium sulfate and reading optical densities at 280 nm; mg/mL = O.D. 280 × dilution factor divided by 1.41 extinction coefficient.
[2]Specific antibody titers determined in an indirect ELISA with theophylline-BSA on the solid phase.

EXAMPLE 4

Effect of Medium BTC-28101 on Cell Growth, Viability and IgG Production

Hybridoma cell line DI16 (anti-*Dirofilaria immitis*) was cultured in either BTC-28101 or DMEM. Cell line DI16 produced higher concentrations of antibody in BTC-28101 than in the in-house formulation of DMEM. Table V shows that D116 cell numbers and cell viability were also higher in BTC-28101.

TABLE V

DI16 Batch Culture: Cell Counts and Viabilities

| TIME | MEDIUM | CELL COUNT | VIABILITY |
|---|---|---|---|
| $D_0$ | BTC-28101 | $2 \times 10^5$/mL | 98% |
|  | DMEM | $2 \times 10^5$/mL | 98% |
| $D_3$ | BTC-28101 | $7.2 \times 10^5$/mL | 83% |
|  | DMEM | $8.4 \times 10^5$/mL | 99% |
| $D_4$ | BTC-28101 | $5.4 \times 10^6$/mL | 57% |
|  | DMEM | $1.5 \times 10^6$/mL | 26% |
| $D_5$ | BTC-28101 | $5.4 \times 10^6$/mL | 58% |
|  | DMEM | $1.5 \times 10^6$/mL | 8% |
| $D_6$ | BTC-28101 | $3.9 \times 10^5$/mL | 30% |
|  | DMEM |  | 0% |
| $D_7$ | BTC-28101 | $3.5 \times 10^5$/mL | 21% |
|  | DMEM |  | 0% |
| $D_8$ | BTC-28101 | $1.8 \times 10^5$/mL | 10% |
|  | DMEM |  | 0% |

Table VI reports comparative Ig titers and concentration in the DI16 cell cultures.

TABLE VI

DI16 Batch Culture: Ig Titers and Concentrations

| TIME | MEDIUM | Ig TITER[1] | Ig mg/mL[2] |
|---|---|---|---|
| $D_3$ | BTC-28101 | 1:1,024 | 1.09 |
|  | DMEM | 1:256 | 0.770 |
| $D_4$ | BTC-28101 | 1:2,048 | 0.882 |
|  | DMEM | 1:512 | 0.926 |
| $D_5$ | BTC-28101 | 1:2,048 | 0.940 |
|  | DMEM | 1:512 | 0.654 |
| $D_6$ | BTC-28101 | 1:2,048 | 1.28 |
|  | DMEM | 1:512 | 0.746 |
| $D_7$ | BTC-28101 | 1:2,048 | 1.11 |
|  | DMEM | Culture terminated | Culture terminated |
| $D_8$ | BTC-28101 | 1:2,048 | 1.39 |
|  | DMEM | Culture terminated | Culture terminated |

[1]Ig titers determined by titrating samples in a mouse Ig capture ELISA.
[2]Ig concentrations determined by precipitating each sample with saturated ammonium sulfate and reading optical densities at 280 nm; mg/mL = O.D. 280 × dilution factor divided by 1.41 extinction coefficient.

EXAMPLE 5

Effect of Medium BTC-28101 on Cell Growth, Viability and Ig Production

Hybridoma cell line NP11 (anti-N-acetylprocainamide) was cultured in either BTC-28101 or DMEM. This cell line was slightly slower than the other cell lines to respond to BTC-28101 with enhanced levels of antibody production (see Table VIIB); variations for different cell lines are not surprising. It is significant that the BTC-28101 culture produced substantial levels of antibody when cultures in DMEM were no longer viable (see Table VIIA). The ability to keep cultures producing for longer periods of time is a significant advantage of BTC-28101.

TABLE VIIA

NP11 Batch Culture: Cell Counts and Viabilities

| TIME | MEDIUM | CELL COUNT | VIABILITY |
|---|---|---|---|
| $D_0$ | BTC-28101 | $2 \times 10^5$/mL | 100% |
|  | DMEM | $2 \times 10^5$/mL | 100% |
| $D_1$ | BTC-28101 | $1.4 \times 10^5$/mL | 100% |
|  | DMEM | $2.3 \times 10^5$/mL | 100% |
| $D_3$ | BTC-28101 | $8 \times 10^5$/mL | 98% |
|  | DMEM | $1.04 \times 10^6$/mL | 84% |
| $D_4$ | BTC-28101 | $8.4 \times 10^5$/mL | 72% |
|  | DMEM | $6.7 \times 10^5$/mL | 21% |
| $D_5$ | BTC-28101 | $1.2 \times 10^6$/mL | 72% |
|  | DMEM | $2.9 \times 10^5$/mL | 21% |
| $D_6$ | BTC-28101 | $8.4 \times 10^5$/mL | 52% |
|  | DMEM | $1 \times 10^5$/mL | 0% |
| $D_7$ | BTC-28101 | $7.6 \times 10^5$/mL | 41% |
|  | DMEM |  | 0% |
| $D_{10}$ | BTC-28101 | $1.3 \times 10^5$/mL | 5% |
|  | DMEM |  | 0% |

TABLE VIIB

NP11 Batch Culture: Ig Titers and Concentrations

| TIME | MEDIUM | Ig TITER[1] | Ig mg/mL[2] |
|---|---|---|---|
| $D_0$ | BTC-28101 | 1:64 | 0.616 |
|  | DMEM | 1:64 | 0.542 |
| $D_1$ | BTC-28101 | 1:16 | 0.590 |
|  | DMEM | 1:16 | 0.488 |
| $D_3$ | BTC-28101 | 1:256 | 0.682 |
|  | DMEM | 1:256 | 0.659 |

TABLE VIIB-continued

NP11 Batch Culture: Ig Titers and Concentrations

| TIME | MEDIUM | Ig TITER[1] | Ig mg/mL[2] |
|---|---|---|---|
| $D_4$ | BTC-28101 | 1:512 | 0.629 |
|  | DMEM | 1:256 | 0.730 |
| $D_5$ | BTC-28101 | 1:512 | 0.930 |
|  | DMEM | 1.256 | 0.777 |
| $D_6$ | BTC-28101 | 1:512 | 0.793 |
|  | DMEM | 1:256 | 0.887 |
| $D_7$ | BTC-28101 | 1:1,024 | 1.300 |
|  | DMEM | — | — |
| $D_{10}$ | BTC-28101 | 1:1,024 | 1.240 |
|  | DMEM | — | — |

[1]Ig titers determined by titrating samples in an indirect ELISA with N-acetylprocainamide-BSA on the solid phase.
[2]Ig concentrations determined by precipitating each sample with saturated ammonium sulfate and reading optical densities at 280 nm; mg/ml = O.D. 280 × dilution factor divided by 1.41 extinction coefficient.

EXAMPLE 6

Effect of BTC-28101 on IgG Production in Hollow Fiber Culture

Performance of the hybridoma cell line TH12 in a "mini" hollow fiber bioreactor (UniSyn Technologies, Inc.'s "Mini Mouse" bioreactor) cultured in FBS supplemented BTC-28101 was compared with the control FBS supplemented DMEM. The results are shown in Table VIII. Comparable levels of antibody were produced by this hybridoma in the control DMEM and in BTC-28101. However, the control culture was terminated after day 13 when viability was <10%. In distinction, the cells maintained in BTC-28101 remained highly viable, and the culture was terminated only because of shortage of medium supply.

TABLE VIII

Comparison of Ig Titer of Hollow Fiber Culture in BTC-28101 and Control DMEM Media

| TIME | BTC-28101 | DMEM |
|---|---|---|
| $D_2$ | 1:6,400 | 1:51,200 |
| $D_5$ | 1:102,400 | 1:204,800 |
| $D_7$ | 1:204,800 | 1:204,800 |
| $D_9$ | 1:204,800 | 1:102,400 |
| $D_{12}$ | 1:204,800 | 1:102,400 |
| $D_{14}$ | 1:204,800 | — |
| $D_{16}$ | 1:102,400 | — |
| $D_{19}$ | 1:51,200 | — |

EXAMPLE 7

BTC-28101 Medium—Hollow Fiber Bioreactors

Figure 2A:
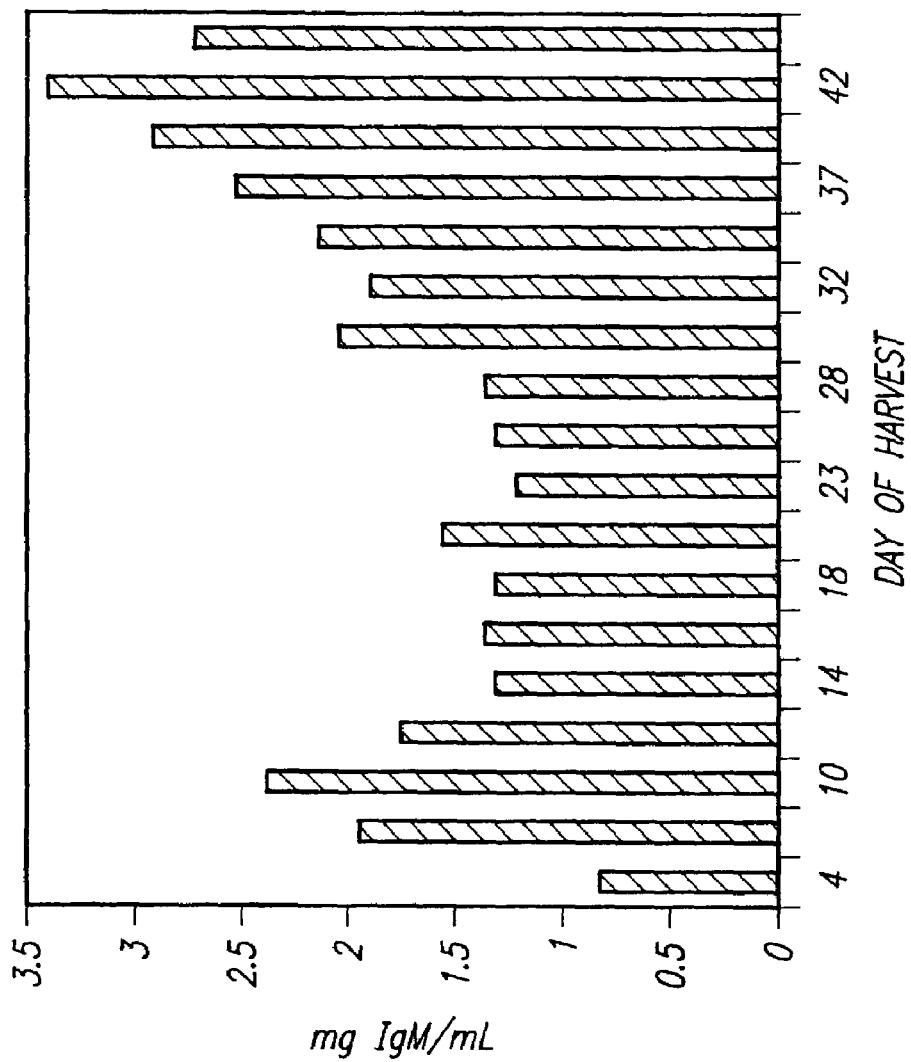
Figure 2B:
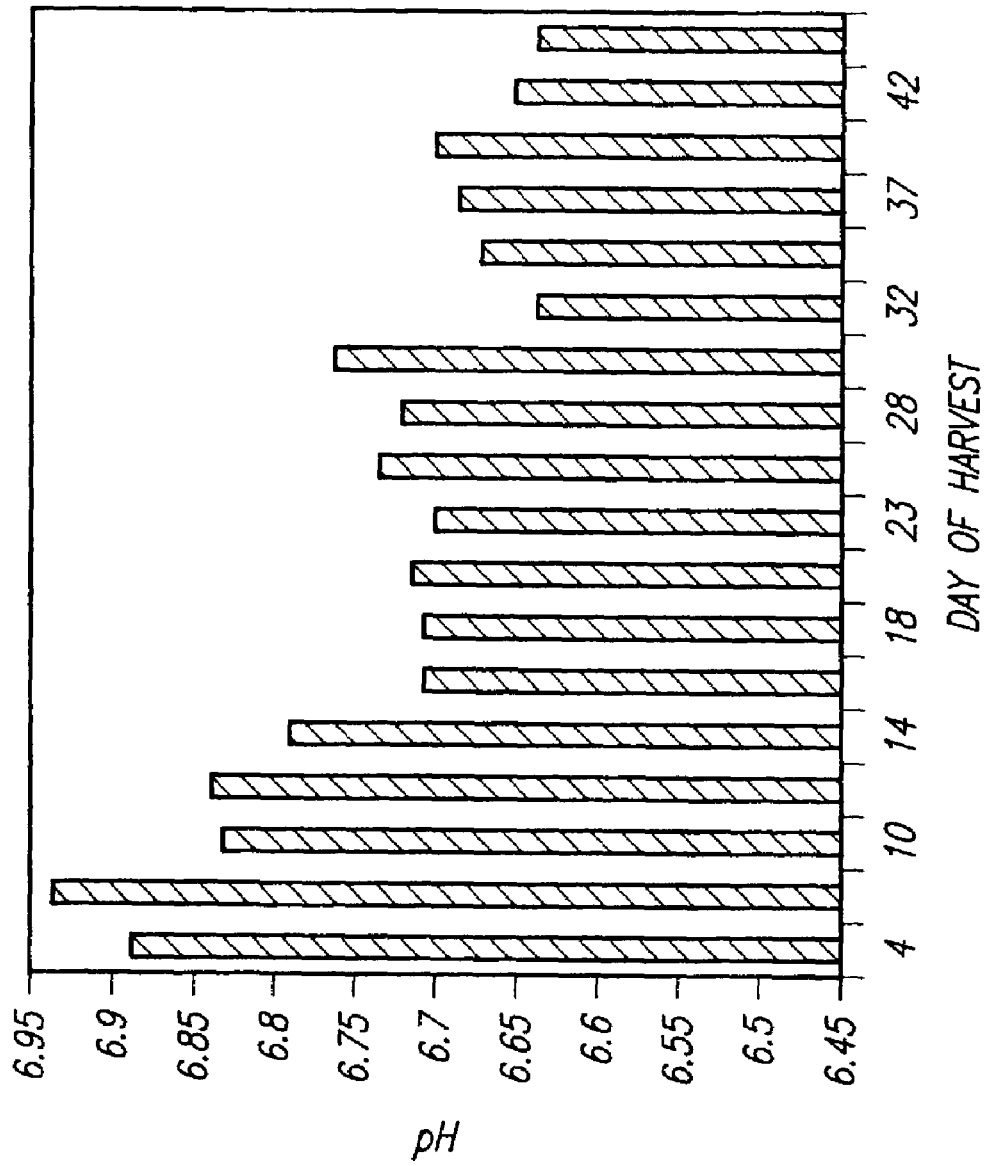
Figure 2C:
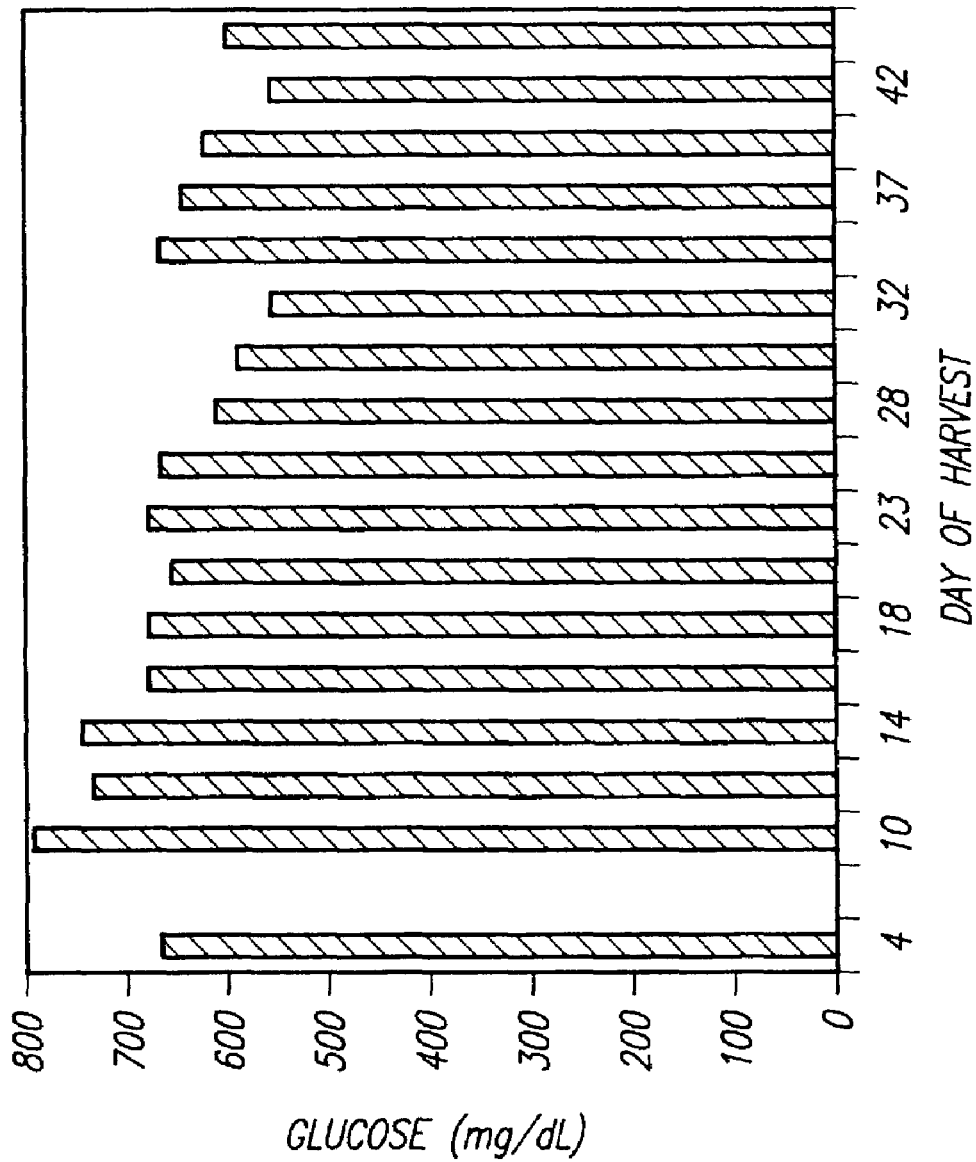

This hollow fiber bioreactor example utilized a particular cell line GBI (Goodwin Biotech, Florida) that normally produces a few hundred μg/mL of MAB in conventional culture methods. FIG. 2A indicates that this cell line performed substantially better in BTC-28101. Data for pH of the medium (FIG. 2B), glucose utilization (FIG. 2C), and cell viability (FIG. 2D) are presented. Cells growing in BTC-28101 in hollow fiber bioreactors do not appear to utilize glucose from the medium at the rate normally seen with conventional media. Monitoring glucose utilization is a standard means of monitoring the progress of cells in bioreactors; ordinarily the higher the level of glucose utilization, the better the cells are growing. When using the medium BTC-28101, this rule does not appear to apply.

EXAMPLE 8

BTC-28101 Medium—Spinner Flask Culture

Anti-theophylline hybridoma cells were inoculated into 250 mL of Difco's preparation of BTC-28101 or DMEM at $2 \times 10^5$ cells/mL in 500 mL spinner flasks. Both media were supplemented with 10% FBS, 2% L-glutamine, and 1% pen-strep. Five mL samples were collected from each flask on the days indicated. Cell viability was determined each day samples were collected, and antibody concentrations were determined for all samples by radial immunodiffusion (RID) after all had been collected. Until that time, the samples (with cell material removed by centrifugation) were stored at −20° C. Antibody concentrations, as determined by RID, and cell viabilities are described in Table IX:

TABLE IX

Comparison of Ig Concentrations and Cell Viabilities in BTC-28101 and DMEM

| | Antibody (μg/mL) | | Cell Viability | |
|---|---|---|---|---|
| TIME | DMEM | BTC-28101 | DMEM | BTC-28101 |
| $D_0$ | <125* | <125 | 95% | 95% |
| $D_1$ | <125 | <125 | 94% | 95% |
| $D_3$ | <125 | <125 | 95% | 95% |
| $D_4$ | <125 | <125 | 58% | 86% |
| $D_7$ | <125 | 176 | 0 | 27% |
| $D_8$ | | 562 | 0 | 21% |
| $D_9$ | | 473 | 0 | 23% |
| $D_{14}$ | | 1,035 | 0 | 19% |

*The lowest concentration RID standard used was 125 μg/mL.

It is significant that the cell line utilized produced 1 mg/mL under conditions described. Specifically, the spinner flasks did not provide ideal culture conditions. Once the culture was established, the medium was never replaced or replenished. Consequently, metabolites and dead cells continued to accumulate.

EXAMPLE 9

BTC-28101 Medium—Spinner Flask Culture

Anti-theophylline hybridoma cells were inoculated into 100 mL of Difco's preparation of BTC-28101 or DMEM at $2 \times 10^5$ cells/mL in 250 mL spinner flasks. All other parameters were as described by Example 8. Antibody concentrations, as determined by RID, and cell viabilities are described in Table X:

TABLE X

Comparison of Ig Concentrations and Cell Viabilities in BTC-28101 and DMEM

| | Antibody (μg/mL) | | Cell Viability | |
|---|---|---|---|---|
| TIME | DMEM | BTC-28101 | DMEM | BTC-28101 |
| $D_0$ | <125* | <125 | 95% | 99% |
| $D_1$ | <125 | 156 | 87% | 99% |
| $D_3$ | <125 | 209 | 49% | 74% |
| $D_4$ | <125 | 436 | 16% | 65% |
| $D_7$ | <125 | 417 | 9% | 39% |
| $D_8$ | <125 | 417 | 0 | 14% |
| $D_9$ | | 400 | 0 | 10% |

*The lowest concentration RID standard used was 125 μg/mL.

Note that the culture volume in Example 9 was one-half that in Example 8. Consequently, nutrients may have depleted more quickly and metabolites or other materials accumulated in inhibitory concentrations more rapidly.

EXAMPLE 10

Effect of BTC-28101 on IgG Production in Serum-Free Culture

This example compares cell growth and monoclonal antibody production in a hybridoma cell line (2HG11) in serum-free BTC-28101 and other commercially available serum-free media available from Gibco.

Figure 3A:
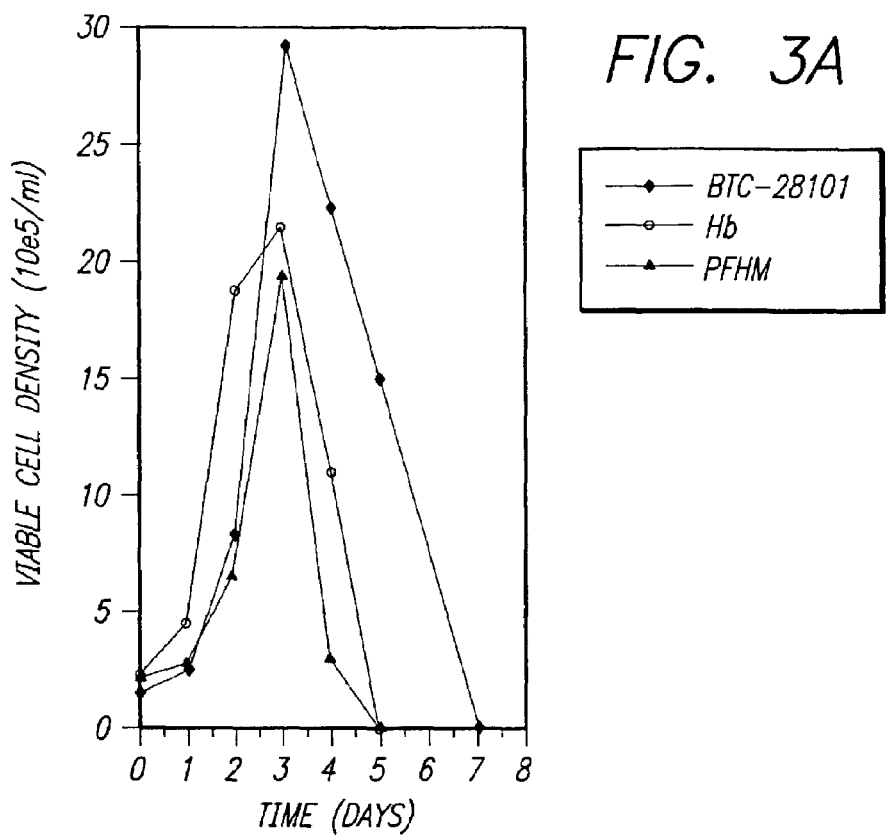
FIGS. 3A-B graphically depict the growth of hybridoma 2HG11 and the production of antibody, wherein FIG. 3A graphically depicts the comparative growth of hybridoma 2HG11 in serum-free BTC-28101 and commercial media Hb and PFHM available from Gibco.
Figure 3B:
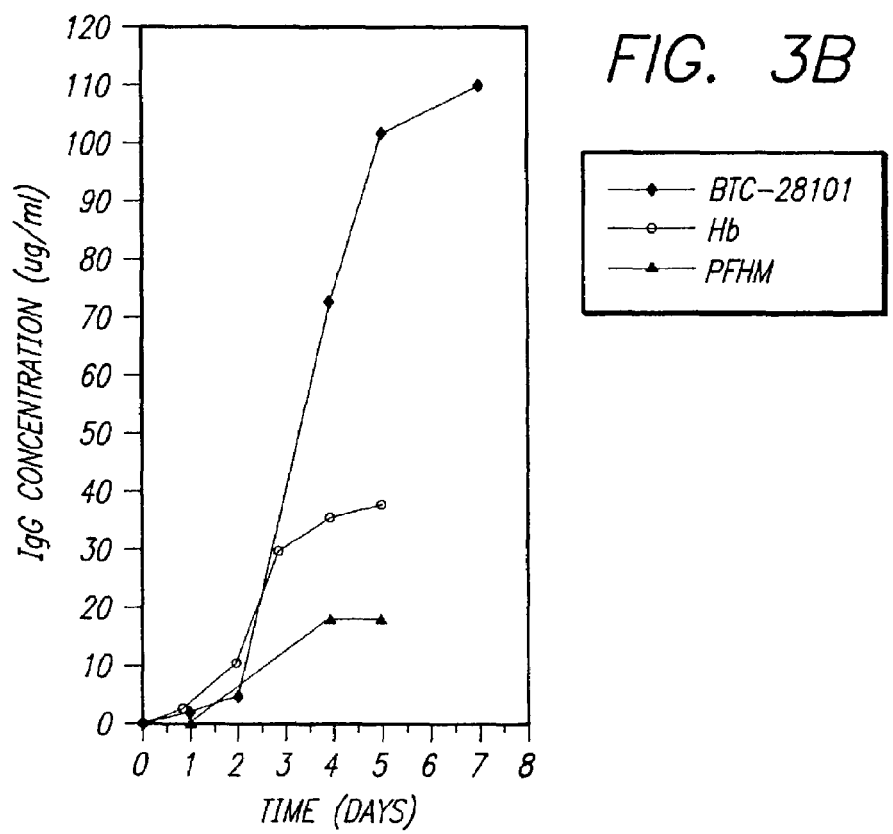

Hybridoma 2HG11 has been adapted to serum-free conditions in the respective media. All media were supplemented with insulin, transferrin, ethanolamine and selenite. Cells were inoculated into 100 mL of BTC-28101 or control media at $2 \times 10^5$ cells/mL in 250 mL shaker flasks. The effects on growth and IgG production are shown in FIGS. 3A and 3B.

EXAMPLE 11

Preparation and Use of BTC-28102 to Culture Hybridomas

The nutrient content of Medium BTC-28101 was further enhanced to formulate medium BTC-28102. To prepare this medium, Component (C) was prepared according to the composition in Table XI and milled to dry fine powder. The powder was sterilized by gamma-irradiation and added to 100 mL of BTC-28101, constituting Medium BTC-28102. The osmolarity of the medium was approximately 400 mOsm.

TABLE XI

Composition of Supplement to Medium BTC-28101 To Make Up BTC-28102 Component (C) in mg

| | |
|---|---|
| Alanine | 2.0 |
| Arginine HCl | 174.4 |
| Asparagine · $H_2O$ | 28.4 |
| Aspartic acid | 12.0 |
| Cystine 2HCl | 31.6 |
| Glutamic acid | 11.9 |
| Glutamine | 299.6 |
| Glycine | 12.8 |
| Histidine HCl · $H_2O$ | 22.6 |
| Hydroxyproline | 9.5 |
| Isoleucine | 47.2 |
| Leucine | 49.6 |
| Lysine HCl | 59.2 |
| Methionine | 14.8 |
| Phenylalanine | 22.3 |
| Proline | 16.6 |
| Serine | 25.5 |
| Threonine | 33.2 |
| Tryptophan | 5.5 |
| Tyrosine | 26.1 |
| Valine | 32.7 |
| Glucose | 3,423 |

Cystine is utilized in lieu of cysteine, which is toxic to cells at high concentration.

The composition of medium BTC-28102 is:
Glucose 10.269 g/L
Amino Acids 15.628 g/L
Amino Acids (% d.w.) 41.1

Figure 4:
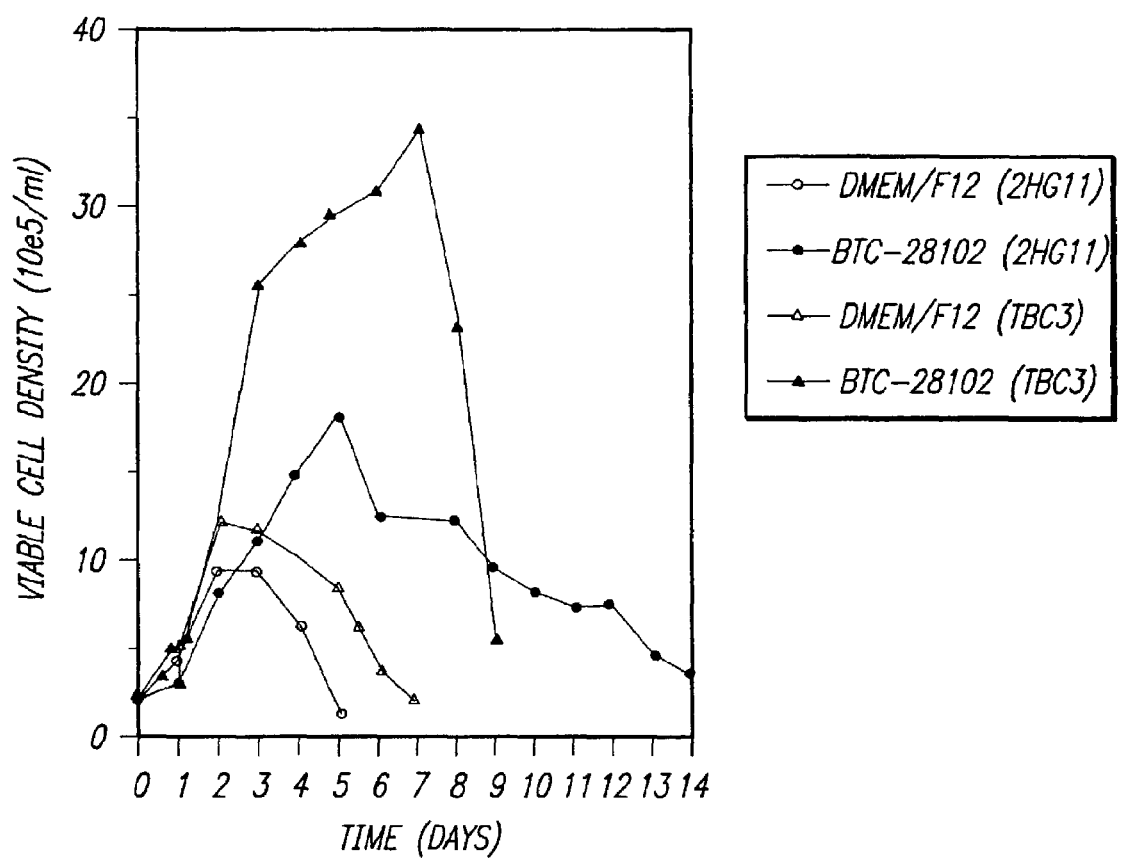
FIG. 4 graphically depicts the comparative growth of hybridomas 2HG11 and TBC3 in medium BTC-28102 of the invention and in control medium DMEM/F12.

Inoculum cells were adapted to Medium BTC-28101 following the protocol stated in Example 2 and inoculated into Medium BYC-28102 at $2 \times 10^5$ cells/mL when starting the 100 mL shaker batch, along with the control cells in 100 mL of DMEM/F12 medium. The effects of the present medium on cell growth are shown in FIG. 4. The maximum concentrations of Ig in the culture are summarized in Table XII.

TABLE XII

Maximum Ig Concentration in the Cultures With BTC-28102 and Control DMEM/F12 Media

| Cell Line | Max Ig Concentration (µg/mL) DMEM/F12 | BTC-28102 |
|---|---|---|
| 2HG11 | 50 | 490 |
| TBC3 | 84 | 1200 |

EXAMPLE 12

Preparation and Use of BTC-28103 to Culture CHO Cells

Figure 5:
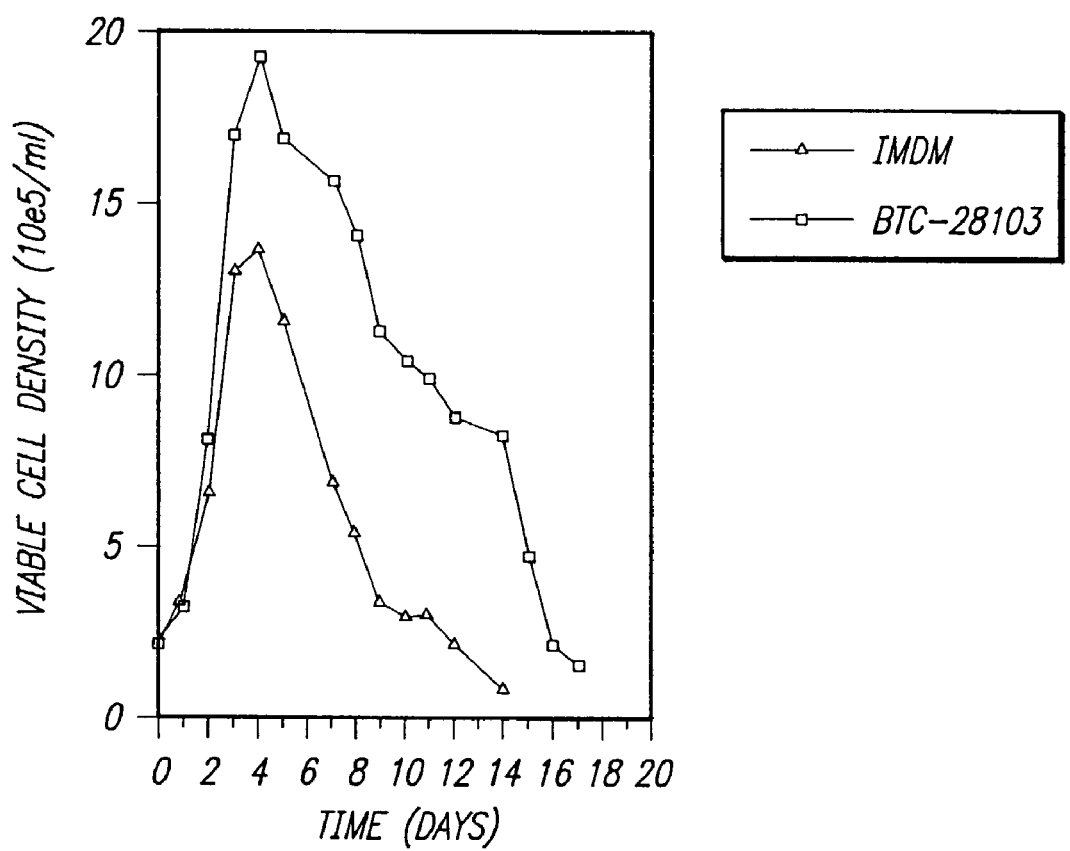
FIG. 5 graphically depicts the comparative growth of CHO cells in medium BTC-28103 of the invention and in control Iscove's Modified Dulbecco's Medium.

This example illustrates use of the invention to culture mammalian cells that express natural or recombinant protein. BTC-28103 was prepared as described in Example 1 for the preparation of BTC-28101 but the buffer contents of HEPES and $NaHCO_3$ were increased to 8330 mg/L and 2650 mg/L, respectively. As a result, the osmolarity of the medium BTC-28103 was approximately 360 mOsm. Chinese hamster ovary (CHO) cells were adapted to grow in suspension and cultured in 100 mL of BTC-28103 and the control Iscove's Modified Dulbecco's Medium (IMDM) in shaker flasks, both supplied with 10% FBS, thymidine and hypoxanthine. Growth of the cultures was followed daily by hemocytometer counting and the results were as presented in FIG. 5.

The media of the invention are useful to culture protein expressing cell lines in the various forms of available bioreactors. In particular, selected media of this invention may be used as the intracapillary medium in hollow fiber bioreactor culture of recombinant protein expressing CHO cells.

EXAMPLE 13

Comparison of Media Constituents

Table XIII compares selected constituents of the compositions of commercially available media RPMI, D/F and eRDF and of the media of the invention BTC-28101 (Example 1) and BTC-28102 (Example 11).

TABLE XIII

| | RPMI | D/F | eRDF | BTC-28101 | BTC-28102 |
|---|---|---|---|---|---|
| Glucose (g/L) | 2.00 | 3.15 | 3.42 | 6.846 | 10.269 |
| Amino acids (g/L) | 1.04 | 1.11 | 3.1 | 6.251 | 15.628 |
| Amino acids (% d.w.) | 5.6 | 6.6 | 16 | 24.8 | 41.1 |

Figure 6:
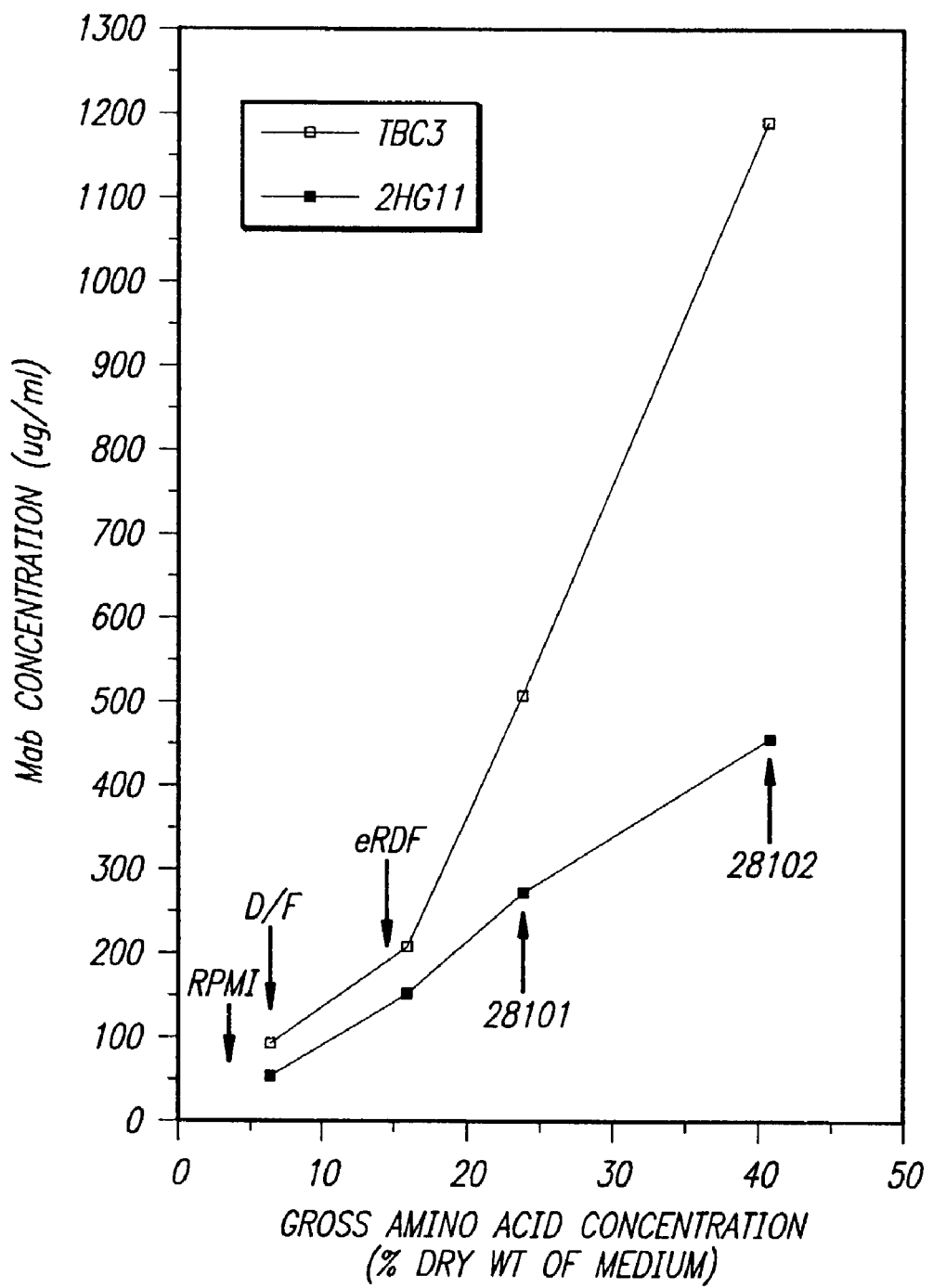
FIG. 6 graphically presents a correlation of percent dry weight of amino acid in the media with MAB production in μg/mL, wherein D/F refers to a 1:1 mixture of Dulbecco's Modified Eagle Medium and Nutrient Mixture F-12 (DMEM/F12).

The correlation of the percent amino acid content in selected media with the MAB production is presented in FIG. 6.

Novel cell culture media which improve the protein production by cells of all types, including mammalian cells which express recombinant protein vectors, have been disclosed. The media of the invention will substantially enhance the cost effectiveness of cell culture procedures generally, including the production of monoclonal antibodies.

All patents and patent applications cited in this specification are hereby incorporated by reference as if they had been specifically and individually indicated to be incorporated by reference.

Although the foregoing invention has been described in some detail by way of illustration and Example for purposes of clarity and understanding, it will be apparent to those of ordinary skill in the art in light of the disclosure that certain changes and modifications may be made thereto without departing from the spirit or scope of the appended claims.

The invention claimed is:

1. A method for culturing animal cells, comprising:
   (a) providing an animal cell;
   (b) providing a cell culture medium at a temperature suitable for growing the animal cell of (a), wherein the medium comprises: 1) a total of from approximately 5.5 to 20 grams per liter of a plurality of amino acids; and 2) at least one carbohydrate; and
   (c) growing the animal cell of (a) in the medium of (b) at said growth temperature, wherein the utilization rate of the carbohydrate source as an energy source by the animal cell is altered as compared to the utilization rate in a conventional medium, thereby culturing cells,
   wherein the cell culture medium comprises the following amino acid components in about the following concentrations expressed as milligrams per liter (mg/L):
   Alanine 13.4;
   Arginine HCl 1,162.90;
   Asparagine-H2O 189.2;
   Aspartic acid 80;
   Cysteine HCl—H$_2$O 105.4;
   Cystine-2HCl 105.4;
   Glutamic acid 79.4;
   Glutamine 1,997.2;
   Glycine 85.6;
   Histidine HCl—H$_2$O 150.9;
   Hydroxyproline 63;
   Isoleucine 314.8;
   Leucine 330.6;
   Lysine HCl 394.6;
   Methionine 98.4;
   Phenylalanine 148.6;
   Proline 110.6;
   Serine 170.2;
   Threonine 221.6;
   Tryptophan 36.8;
   Tyrosine 174; and
   Valine 218; or
   the cell culture medium comprises the following amino acid components in about the following concentrations expressed as milligrams per liter (mg/L):
   Alanine 33.4;
   Arginine HCl 2,906.9;
   Asparagine-H2O 473.2;
   Aspartic acid 200;
   Cysteine HCl—H$_2$O 105.4;
   Cystine-2HCl 421.4;
   Glutamic acid 198.4;
   Glutamine 4,993.2;
   Glycine 213.6;
   Histidine HCl-H$_2$O 376.9;
   Hydroxyproline 158;
   Isoleucine 786.8;
   Leucine 826.6;
   Lysine HCl 986.6;
   Methionine 246.4;
   Phenylalanine 371.6;
   Proline 276.6;
   Serine 425.2;
   Threonine 553.6;
   Tryptophan 91.8;
   Tyrosine 435; and
   Valine 545.

2. The method of claim 1, wherein the cell produces at least one protein of interest and production of the at least one protein of interest is increased relative to the production of the at least one protein of interest produced by the same cell grown in the conventional medium.

3. The method of claim 2, wherein the conventional medium is selected from the group consisting of: DMEM, DMEM/F12, eRDF, and RPMI.

4. The method of claim 1, wherein the cell produces at least one protein of interest and production of the at least one protein of interest is increased at least about two-fold relative to the production of the at least one protein of interest produced by the same cell grown in the conventional medium.

5. The method of claim 1, wherein the cell produces at least one protein of interest and production of the at least one protein of interest is increased at least about five-fold relative to the production of the at least one protein of interest produced by the same cell grown in the conventional medium.

6. The method of claim 1, wherein the cell produces at least one protein of interest and production of the at least one protein of interest is increased at least about ten-fold relative to the production of the at least one protein of interest produced by the same cell grown in the conventional medium.

7. The method of claim 1, wherein the cell remains viable for a longer period of time in continuous culture without the replenishment or exchange of growth medium as compared to the time the same type of cell remains viable when grown in the conventional medium.

8. The method of claim 7, wherein the conventional medium is selected from the group consisting of: DMEM, DMEM/F12, eRDF, and RPMI.

9. The method of claim 1, wherein the cell remains viable for at least twice as long as the same type of cell grown in the conventional medium.

10. The method of claim 1, wherein the cell remains viable for at least five times as long as the same type of cell grown in the conventional medium.

11. The method of claim 2, wherein the cell is a hybridoma cell or a myeloma cell and the at least one protein of interest is an antibody.

12. The method of claim 2, wherein the cell comprises a recombinant protein expression vector and the at least one protein of interest is a recombinant protein expressed by the vector in the cell.

13. The method of claim 12, wherein the cell is a mammalian cell.

14. The method of claim 13, wherein the mammalian cell is selected from the group consisting of a CHO cell, a BHK cell, a COS cell, and a Namalwa cell.

* * * * *